United States Patent
Goto et al.

(10) Patent No.: US 11,030,493 B2
(45) Date of Patent: Jun. 8, 2021

(54) ESTIMATING SEQUENTIAL BLOOD-SUGAR LEVELS USING IMAGES OF MEALS

(71) Applicant: INTERNATIONAL BUSINESS MACHINES CORPORATION, Armonk, NY (US)

(72) Inventors: Takuya Goto, Kodaira (JP); Yutaka Oishi, Kawasaki (JP); Chiaki Oishi, Yokohama (JP); Shuji Umehara, Kawasaki (JP); Masaki Saitoh, Yokohama (JP)

(73) Assignee: International Business Machines Corporation, Armonk, NY (US)

(*) Notice: Subject to any disclaimer, the term of this patent is extended or adjusted under 35 U.S.C. 154(b) by 107 days.

(21) Appl. No.: 16/137,144

(22) Filed: Sep. 20, 2018

(65) Prior Publication Data

US 2020/0097777 A1 Mar. 26, 2020

(51) Int. Cl.
*G06K 9/62* (2006.01)
*G06T 7/00* (2017.01)
*G06N 3/08* (2006.01)
*G16H 50/20* (2018.01)

(52) U.S. Cl.
CPC .......... *G06K 9/6289* (2013.01); *G06K 9/6262* (2013.01); *G06N 3/08* (2013.01); *G06T 7/0012* (2013.01); *G16H 50/20* (2018.01); *G06K 2209/17* (2013.01); *G06K 2209/27* (2013.01); *G06T 2207/20081* (2013.01); *G06T 2207/20084* (2013.01)

(58) Field of Classification Search
CPC .............. G06K 9/6289; G06K 9/6262; G06K 2209/17; G06K 2209/27; G16H 50/20; G06T 7/0012; G06T 2207/20084; G06T 2207/20081; G06N 3/08
See application file for complete search history.

(56) References Cited

U.S. PATENT DOCUMENTS

| | | | |
|---|---|---|---|
| 2013/0038453 A1* | 2/2013 | Nishiyama | A61B 5/14532 340/573.1 |
| 2016/0066843 A1 | 3/2016 | Mensinger et al. | |
| 2017/0173262 A1 | 6/2017 | Veltz | |
| 2017/0216518 A1* | 8/2017 | Davis | G06N 20/00 |
| 2017/0323174 A1* | 11/2017 | Joshi | G06K 9/344 |
| 2018/0330062 A1* | 11/2018 | Balaban | G06N 7/08 |
| 2018/0365577 A1* | 12/2018 | Huang | G06Q 30/0282 |
| 2019/0274624 A1* | 9/2019 | Mazlish | A61B 5/6833 |

OTHER PUBLICATIONS

Mell et al., "The NIST Definition of Cloud Computing," National Institute of Standards and Technology, Sep. 2011, p. 1-3, Special Publication 800-145.

* cited by examiner

*Primary Examiner* — Christopher Wait
(74) *Attorney, Agent, or Firm* — Samuel A Waldbaum

(57) ABSTRACT

A method, computer system, and a computer program product for predicting a variation of sequential blood glucose levels by using deep learning is provided. The present invention may include training a predictor associated with a user by using a deep learning network. The present invention may further include predicting a plurality of sequential blood glucose levels by the trained predictor based on at least one meal image, at least one time-period, and at least one set of data associated with a plurality of blood glucose levels of the user.

21 Claims, 6 Drawing Sheets

US 11,030,493 B2

ESTIMATING SEQUENTIAL BLOOD-SUGAR LEVELS USING IMAGES OF MEALS

BACKGROUND

The present invention relates generally to the field of computing, and more particularly to medical technology.

Conventional techniques for monitoring blood glucose levels include directly measuring the glucose level in blood collected with a blood extracting device (e.g., a syringe, a lancing device) and periodically measuring glucose levels in blood with a continuous glucose monitoring sensor (CGM) attached to the body. However, the use of a blood extracting device or CGM sensor may impose a high physical burden on a patient suffering from diabetes. In addition, conducting a method of measuring the glucose level in blood may require too much time in the case of a diabetic, for whom a rapid increase in the glucose levels is associated with life threatening consequences.

SUMMARY

Embodiments of the present invention disclose a method, computer system, and a computer program product for predicting a variation of sequential blood glucose levels by using deep learning. The present invention may include training a predictor associated with a user by using a deep learning network. The present invention may further include predicting a plurality of sequential blood glucose levels by the trained predictor based on at least one meal image, at least one time-period, and at least one set of data associated with a plurality of blood glucose levels of the user.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
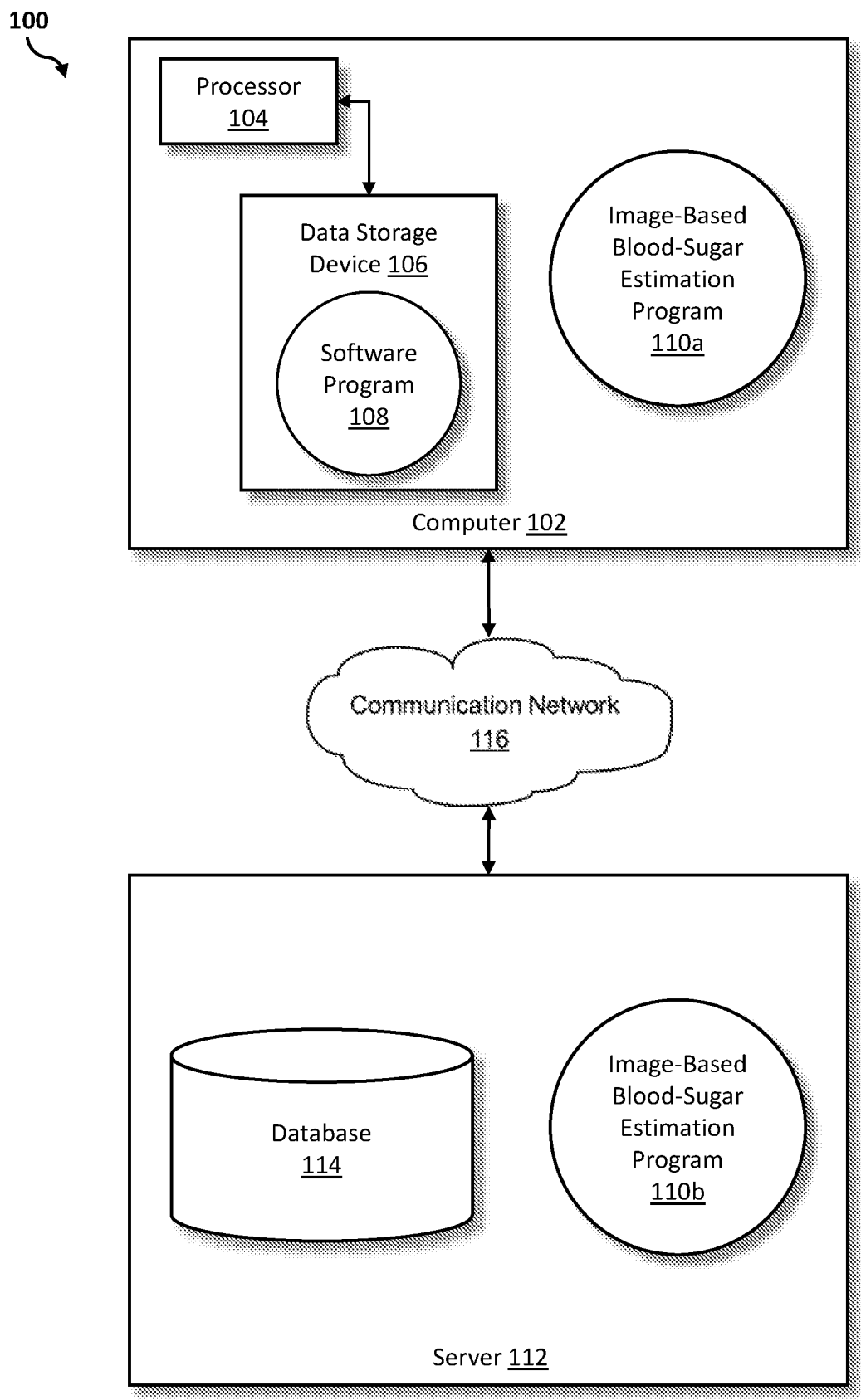
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for predicting a variation of sequential blood glucose levels. As such, the present embodiment has the capacity to improve the technical field of medical technology by utilizing deep learning networks to predict variations of sequential blood glucose levels for a user who consumes a specific meal at a specific time. More specifically, the present embodiment may train a predictor associated with a user by using a deep learning network, and predict a plurality of sequential blood glucose levels by the trained predictor based on at least one meal image, at least one time-period, and at least one set of data associated with a plurality of blood glucose levels of the user.

As previously described, conventional techniques for monitoring blood glucose levels include directly measuring the glucose level in blood collected with a blood extracting device (e.g., a syringe, a lancing device) and periodically measuring glucose levels in blood with a continuous glucose monitoring sensor (CGM) attached to the body. However, the use of a blood extracting device or CGM sensor may impose a high physical burden on a patient suffering from diabetes. In addition, conducting a method of measuring the glucose level in blood may require too much time in the case of a diabetic, for whom a rapid increase in the glucose levels is associated with life threatening consequences.

As such, applying a technique for predicting variation of time-series data solely based on the data (e.g., Recurrent Neural Network based technique) may be conceivable for predicting blood glucose levels. However, the variations of the glucose level in blood may greatly differ depending on the meals. Therefore, prediction of a person's blood glucose levels by this method may be difficult and inaccurate.

Additionally, there is a technique for predicting caloric count of a meal based on an image of the meal. However, using such a technique to predict blood glucose levels in a person may be difficult because the blood glucose level before the meal greatly affects the variation of the blood glucose level after the meal.

Therefore, it may be advantageous to, among other things, predict variation of the sequential blood glucose levels of a person based on an image of a meal and the measured result from the CGM sensor associated with the person, using deep learning.

According to at least one embodiment, the image-based blood-sugar estimation program may include a training phase. During the training phase, a predictor may be trained to predict sequential blood glucose levels based on an image of a meal, time and data generated by a CGM sensor associated with the particular person (i.e., user).

According to at least one embodiment, the image-based blood-sugar estimation program may include a prediction phase. During the prediction phase, the image-based blood-sugar estimation program may predict the sequential blood glucose levels based on the image of a meal associated with the user, and the CGM data associated with the user.

According to at least one embodiment, the image-based blood-sugar estimation program may utilize previously predicted data, instead of the CGM sensor data, when the CGM sensor data is unavailable.

According to at least one embodiment, the image-based blood-sugar estimation program may be utilized for cases where the measurement data via blood collection with a blood extracting device, or CGM sensor, is unavailable. However, the users for this embodiment may exclude diabetics.

According to at least one embodiment, the image-based blood-sugar estimation program may be utilized to predict blood glucose levels, as well as sequential numerical values that vary depending on meals, such as alcohol content or lactic acid content in a person's blood.

According to at least one embodiment, the image-based blood-sugar estimation program may include two phases: a training phase and a prediction phase. The output of the training phase, which estimates the factor of a meal, may be utilized as input into the prediction phase, which predicts a blood glucose level sequentially. In the present embodiment, both phases (i.e., training and prediction phases) may be trained entirely in a deep learning framework.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and an image-based blood-sugar estimation program 110a. The networked computer environment 100 may also include a server 112 that is enabled to run an image-based blood-sugar estimation program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 4, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the image-based blood-sugar estimation program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the image-based blood-sugar estimation program 110a, 110b (respectively) to estimate glucose levels in a person's blood by utilizing images associated with meals. The image-based blood-sugar estimation method is explained in more detail below with respect to FIGS. 2 and 3.

Figure 2:
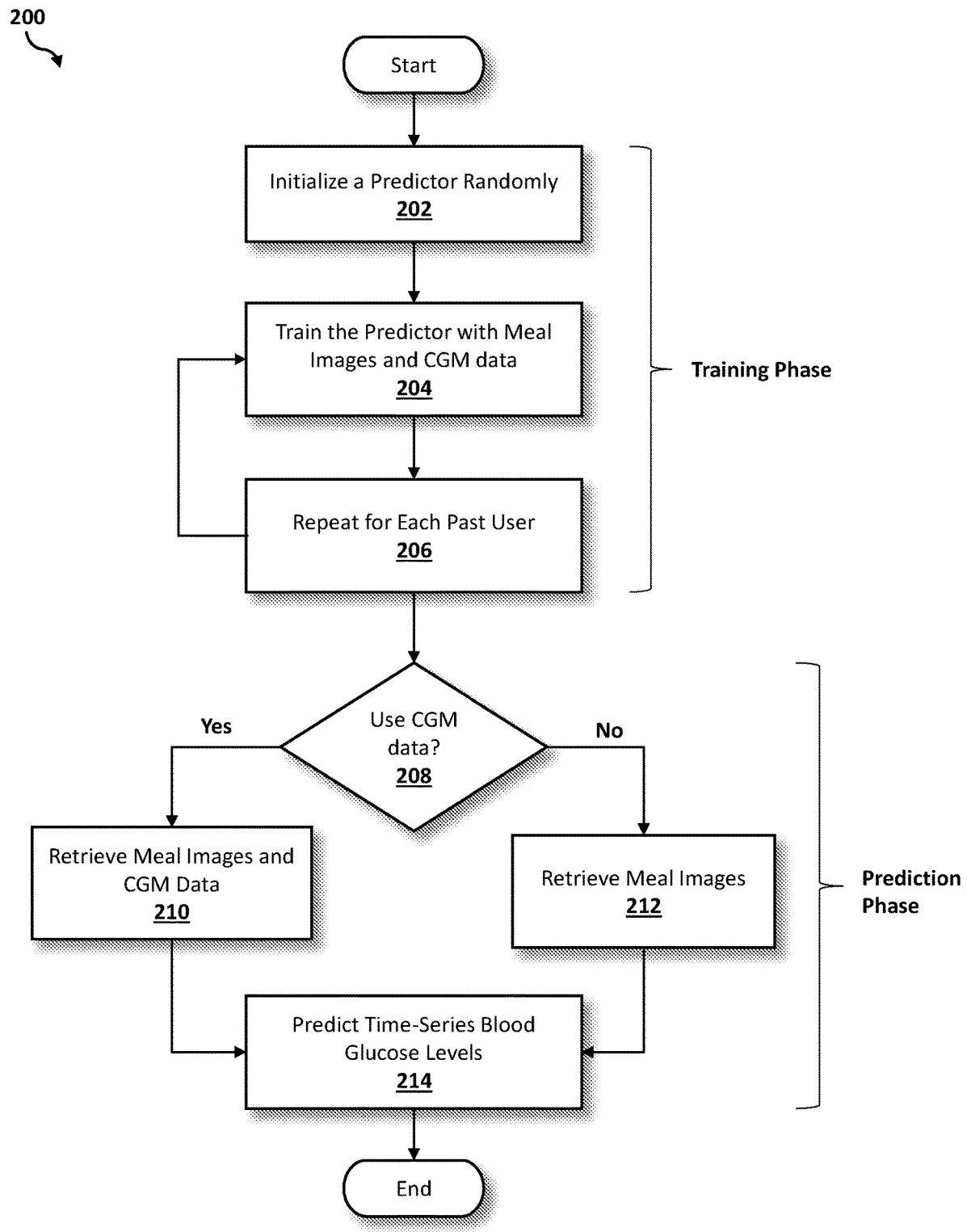
FIG. 2 is an operational flowchart illustrating a process for estimating blood glucose levels utilizing meal images according to at least one embodiment.

Referring now to FIG. 2, an operational flowchart illustrating the exemplary image-based blood-sugar estimation process 200 used by the image-based blood-sugar estimation program 110a, 110b according to at least one embodiment is depicted.

At 202, a predictor is randomly initialized. During the training phase, the image-based blood-sugar estimation program 110a, 110b may utilize a set of training data (i.e., past users) to initialize and normalize the predictor to improve the accuracy of the predictor, when predicting time-series blood glucose levels based on the time that a user consumed a certain meal. First, the image-based blood-sugar estimation program 110a, 110b may initialize the predictor. The predictor may be utilized to predict blood glucose levels based on recurrent neural network (RNN) variables (e.g., weights associated with RNN) and convolutional neural network (CNN) variables (e.g., filters associated with CNN). The image-based blood-sugar estimation program 110a, 110b may utilize various methods to randomly initialize the predictor. The weights and filters, for example, are randomly initialized based on a normal distribution with mean 0 and standard 1, and therefore, the training data received as input would be normalized based on a mean of 0 and standard of 1. In another example, the predictor is initialized based on a uniform distribution (e.g., Zeros, Ones, Constant, RandomNormal, RandomUniform, TruncatedNormal, VarianceScaling, Orthogonal, Identity, LeCun_uniform, Glorot_normal or Xavier normal, Glorot_uniform or Xavier uniform, He_normal, LeCun_normal, He_uniform). The more training data utilized to train the predictor, the greater the accuracy of the trained predictor, and therefore, the better the functionality of the image-based blood-sugar estimation program 110a, 110b.

For example, the image-based blood-sugar estimation program 110a, 110b selects previous data associated with past users, who have a close familial relationship with User A. The data includes nine different blood glucose levels with corresponding meals associated with User A's parents and two siblings. The data is then utilized by the image-based blood-sugar estimation program 110a, 110b that generates a predictor with a normal distribution based on the Random-Normal initialization method.

Next, at 204, the predictor is trained with meal images and continuous glucose monitoring (CGM) data. The image-based blood-sugar estimation program 110a, 110b may utilize meal images to represent the specific meals and continuing glucose monitoring (CGM) data of numerous users to train the predictor. Using a software program 108 on the user device (e.g., user computer 102), the user may upload meal images associated with the meal consumed by a past user along with the CGM data (i.e., the blood glucose levels based on milligrams per deciliter for the past user at or near the time that the past user consumed the meal depicted by the meal images) associated with the same past user via a communications network 116. The training data may be received as input into a deep learning network (e.g., recurrent neural network (RNN) and convolutional neural network (CNN)). A detailed operational flowchart explaining the use of CNN and RNN in the image-based blood-sugar estimation program 110a, 110b will be described in greater detail below with respect to FIG. 3.

In another embodiment, the meal images may be uploaded via a communications network 116 from social media posts, a camera associated with the user device (e.g., smart phone), an application associated with the user device, or an image from a restaurant's website or online menu.

In at least one embodiment, the image-based blood-sugar estimation program 110a, 110b may present an error message if the image-based blood-sugar estimation program 110a, 110b is unable to recognize the meal depicted by the meal image. The image-based blood-sugar estimation program 110a, 110b may then prompt the user to provide additional information associated with the meal image uploaded onto the image-based blood-sugar estimation program 110a, 110b. For example, the image-based blood-sugar estimation program 110a, 110b may prompt the user (e.g., a dialog box) to provide additional information regarding the name of the meal (e.g., cheese hamburger with Cajun fries), the estimated calories of the meal (if known by the user), the size of the meal, where the meal was prepared (e.g., if the meal was prepared at a restaurant, the user can provide the name of the restaurant), how much of the meal did the user consume (e.g., if the user consumed half the cheeseburger and all the Cajun fries), and whether any condiments were added to the meal.

In at least one embodiment, the image-based blood-sugar estimation program 110a, 110b may prompt the user (e.g., via dialog box) to provide the CGM data associated with the meal images uploaded by the user. Once the image-based blood-sugar estimation program 110a, 110b retrieves the meal images by the user, the image-based blood-sugar estimation program 110a, 110b may, for example, prompt the user via a dialog box stating to provide the CGM data associated with the user who consumed the meal. Then, the image-based blood-sugar estimation program 110a, 110b may prompt the user to provide the time when the CGM data was taken. For example, in the first dialog box, the user includes the following CGM data: First CGM Reading: 110 mg/dl; Second CGM Reading: 90 mg/dl; and Third CGM Reading: 70 mg/dl. Then, the image-based blood-sugar estimation program 110a, 110b prompts the user to provide the times associated with each reading. As such, the user provides the following times to the corresponding readings: 12:18 PM for the first CGM reading; 1:25 PM for the second CGM reading; and 3:35 PM for the third CGM reading.

In at least one embodiment, the image-based blood-sugar estimation program 110a, 110b may upload the CGM data from a blood glucose monitoring or measuring device (e.g., a glucometer) (including a continuous blood glucose monitoring device). The blood glucose monitoring or measuring device may be connected to the user device via a communications network. As such, the user may be able to upload the new CGM data directly from the blood glucose monitoring or measuring device. In another embodiment, the blood glucose monitoring or measuring device may prompt the user device that CGM data has been received. The image-based blood-sugar estimation program 110a, 110b may prompt the user (e.g., via dialog box) to indicate whether the user has consumed a meal for which at least one meal image may have to be uploaded into the image-based blood-sugar estimation program 110a, 110b.

In another embodiment, the image-based blood-sugar estimation program 110a, 110b may include biometric sensors (e.g., a CGM data sensor) connected to the blood glucose monitoring or measuring device to detect additional CGM data associated with a specific user. Such CGM data sensors may be utilized to upload the CGM data associated with the user. In addition, the image-based blood-sugar estimation program 110a, 110b may utilize a camera to prompt the user to indicate whether the user has eaten a particular meal and the estimated time of such meal, if the user device detects that the user took a photo or image associated with a meal on the user device.

In another embodiment, depending on whether the meal images taken by a camera associated with the user include a time-stamp for each image, the image-based blood-sugar estimation program 110a, 110b may prompt the user with a suggested time for when the user may have consumed the meal.

In another embodiment, the user may manually upload the CGM data and meal images into the image-based blood-sugar estimation program 110a, 110b. The user may, for example, click the "Manual Entries" button displayed on the bottom of the main screen of the image-based blood-sugar estimation program 110a, 110b. The user will then be prompted to include an image associated with a meal consumed by the user, as well as the CGM data and the time that each blood glucose level associated with the CGM data was taken. The user may then click the "Submit" button located at the bottom of the dialog box. The image-based blood-sugar estimation program 110a, 110b may then prompt the user to indicate whether the CGM data and meal images were successfully retrieved. If the retrieval was unsuccessful, then the image-based blood-sugar estimation program 110a, 110b may prompt the user to re-enter the necessary information.

Continuing the previous example, User A uploads several meal images of a fish sandwich with a garden salad and a chocolate milkshake that the user ate for dinner from 5:39 PM to 6:15 PM. After uploading the meal images, the image-based blood-sugar estimation program 110a, 110b prompts User A to provide the estimated time when the meal was eaten, and the User A inputs 6:15 PM, the time that User A finished the meal. User A then uploads the blood glucose levels measured by the User A's continuous blood glucose level monitoring device, which is 73 mg/dl at 7:15 PM (t−3), 72 mg/dl at 7:55 PM (t−2) and 70 mg/dl at 8:30 PM (t−1).

Then, at 206, the training phase is repeated for each past user. The image-based blood-sugar estimation program 110a, 110b may prepare past users (i.e., training data) for the predictor prior to the commencement of the training phase. The image-based blood-sugar estimation program 110a, 110b may repeat the initialization of the predictor with each set of training data (i.e., past users) to improve the accuracy of the predictor.

In at least one embodiment, the image-based blood-sugar estimation program 110a, 110b may categorize the past users based on the relationship of each user. For example, family members may be included in the training data (i.e., past users) to improve accuracy with predicting time series blood glucose levels of a user with a similar genealogical composition, or a certain demographic may be included in the training data to improve accuracy amongst persons with one or more common traits (e.g., location, age, race, height, weight, gender, occupation, ethnic group, eating habits, stress levels).

Continuing the previous example, User A and several of User A's close family members, including spouse, parents and three adult children, are utilizing the image-based blood-sugar estimation program 110a, 110b. Therefore, the image-based blood-sugar estimation program 110a, 110b may perfect the training of the predictor by training the predictor based on similar CGM data and meal images from User A's close family members.

Then, at 208, the image-based blood-sugar estimation program 110a, 110b determines whether CGM data is used. During the prediction phase, the image-based blood-sugar estimation program 110a, 110b may utilize the trained predictor to predict the time-series blood glucose levels for a specific user. Since the user provides the meal images, CGM data and the time to the image-based blood-sugar estimation program 110a, 110b, the image-based blood-sugar estimation program 110a, 110b determines whether corresponding CGM data was received by the user with a specific meal image for a specific time.

Continuing the previous example, the image-based blood-sugar estimation program 110a, 110b may determine whether User A provided CGM data associated with the meal images provided of the fish sandwich, garden salad and chocolate milkshake consumed by User A for dinner at 6:15 PM.

If the image-based blood-sugar estimation program 110a, 110b determines that CGM data is used at 208, then the meal images and CGM data are retrieved at 210. If the user provided the meal images and corresponding CGM data for a specific time, then the image-based blood-sugar estimation program 110a, 110b may retrieve the meal images (i.e., meal images which the CNN already extracted features of and output a corresponding T-dimensional vector) and the corresponding CGM data (i.e., S-dimensional vector). The retrieved meal images (i.e., T-dimensional vector) and the retrieved CGM data (i.e., S-dimensional vector) may be merged to predict the time-series blood glucose levels for each user.

Continuing the previous example, the image-based blood-sugar estimation program 110a, 110b determines that User A provided CGM data corresponding with the meal images uploaded into the image-based blood-sugar estimation program 110a, 110b for each time-period (t−1, t−2, and t−3) and utilizes the meal images and CGM data to determine the blood glucose levels for User A at t and t+1.

If, however, the image-based blood-sugar estimation program 110a, 110b determines that CGM data is not used at 208, then the meal images are retrieved at 212. Without the CGM data, the image-based blood-sugar estimation program 110a, 110b may utilize the meal images alone for a specific time to predict the time-series blood glucose levels for each user.

In at least one embodiment, the CGM data previously provided and the meal images uploaded by the user may be stored in separate databases (e.g., database 114) and, when necessary, selected and uploaded by the image-based blood-sugar estimation program 110a, 110b.

Continuing the previous example, if User A did not provide CGM data, the image-based blood-sugar estimation program 110a, 110b may use the meal images of the fish sandwich, garden salad and chocolate milkshake, as well as any past blood glucose levels to generate predicted blood glucose levels for each time-period (t−1, t−2, and t−3) to determine the blood glucose levels for User A at t and t+1.

Then, at 214, the time-series blood glucose levels are predicted. Regardless of whether the meal images and CGM data are retrieved at 210, or the meal images are retrieved at 212, the image-based blood-sugar estimation program 110a, 110b may predict the time-series glucose levels associated with each user by utilizing deep learning, namely CNN and RNN. A detailed operational flowchart explaining the use of CNN and RNN in the image-based blood-sugar estimation program 110a, 110b will be described in greater detail below with respect to FIG. 3.

In at least one embodiment, the image-based blood-sugar estimation program 110a, 110b may display, on the screen of the user device, the predicted blood glucose levels at t and t+1 for the specific user. In at least one embodiment, the image-based blood-sugar estimation program 110a, 110b may include the predicted blood glucose levels at t and t+1 on an application for the user to provide to a physician or medical professional (e.g., endocrinologist, nutritionist, dietician, primary care physician) associated with the user. Such data may be utilized to adjust medication, diets or exercise plans associated with the user.

In at least one embodiment, the image-based blood-sugar estimation program 110a, 110b may alert (e.g., via previously determined sound emitted by the user device, or prompt by dialog box) the user that the predicted blood glucose levels (t or t+1) may fall outside of a previously determined normal range level (i.e., lower than or higher than) for the user. For example, the user clicks the "Settings" button on the bottom of the main screen. A second screen appears in which the user clicks the "Normal Range" button on the second screen. A dialog box then appears in which the user enters the normal range of the blood glucose levels for the user, and at the bottom of the dialog box is a statement indicating that the image-based blood-sugar estimation program 110a, 110b may alert the user if the predicted blood glucose levels associated with the user fall outside the normal range indicated by the user. If the user clicks the box next to that statement, then the image-based blood-sugar estimation program 110a, 110b will alert the user when the predicted blood glucose levels fall outside of the indicated normal range. If the user does not click that box next to that statement, then the image-based blood-sugar estimation program 110a, 110b will not notify the user.

In at least one other embodiment, the user may have previously selected a physician or medical professional, a person closely related to the user (e.g., spouse, friend, parent, close family member) or health care proxy agent (e.g., a person delegated by the user to make medical decisions on the user's behalf in case of medical incapacitation) to send such an alert message to as well as the user. As such, the physician or medical professional may be contemporaneously informed of the user's predicted blood glucose levels, and may immediately advise the user. In addition, the person closely related to the user or the health care proxy agent may be informed of the user's health in the case of an emergent situation. The user may previously delegate the medical professional, the closely related person and the health care proxy agent when initially setting up the personal settings or profile for the image-based blood-sugar estimation program 110a, 110b. The user may change the delegation for the medical professional, the closely related person and the health care proxy agent at any time by clicking, for example, the "Alert" button located on the bottom right side of the main screen of the image-based blood-sugar estimation program 110a, 110b.

Continuing the previous example, the image-based blood-sugar estimation program 110a, 110b predicts the time-series blood glucose levels (t and t+1) associated with User A based on the training data, namely CGM data associated with User A and the CGM data associated with User A's close family members, and the meal images corresponding with the past and current CGM data. The image-based blood-sugar estimation program 110a, 110b displays 80 mg/dl as the predicted blood glucose level at t, and 90 mg/dl as the predicted glucose level at t+1.

In at least one embodiment, the image-based blood-sugar estimation program 110a, 110b may store the CGM data (t−1, t−2, t−3), the predicted blood glucose levels (t and t+1) and the meal images into a database (e.g., database 114). The database may be further indexed based on the specific user associated with the predicted blood glucose levels, or the severity level of the predicted blood glucose levels.

In another embodiment, the user may provide feedback to the image-based blood-sugar estimation program 110a, 110b if the user determines that the predicted blood glucose levels are erroneous, or the meal images may have to be further explained for the image-based blood-sugar estimation program 110a, 110b to provide accurate predicted blood glucose levels for the user. The image-based blood-sugar estimation program 110a, 110b may then determine whether the received feedback affects the trained predictor. If the feedback affects the trained predictor, then the feedback may be utilized and incorporated into the training phase of the trained predictor to improve the accuracy of the trained predictor, and the overall functionality of the image-based blood-sugar estimation program 110a, 110b. If not, the feedback may be ignored by the image-based blood-sugar estimation program 110a, 110b. In at least one embodiment, the received feedback may be stored in a database (e.g., database 114) by the image-based blood-sugar estimation program 110a, 110b for a previously determined period of time, and then permanently deleted from the image-based blood-sugar estimation program 110a, 110b.

Figure 3:
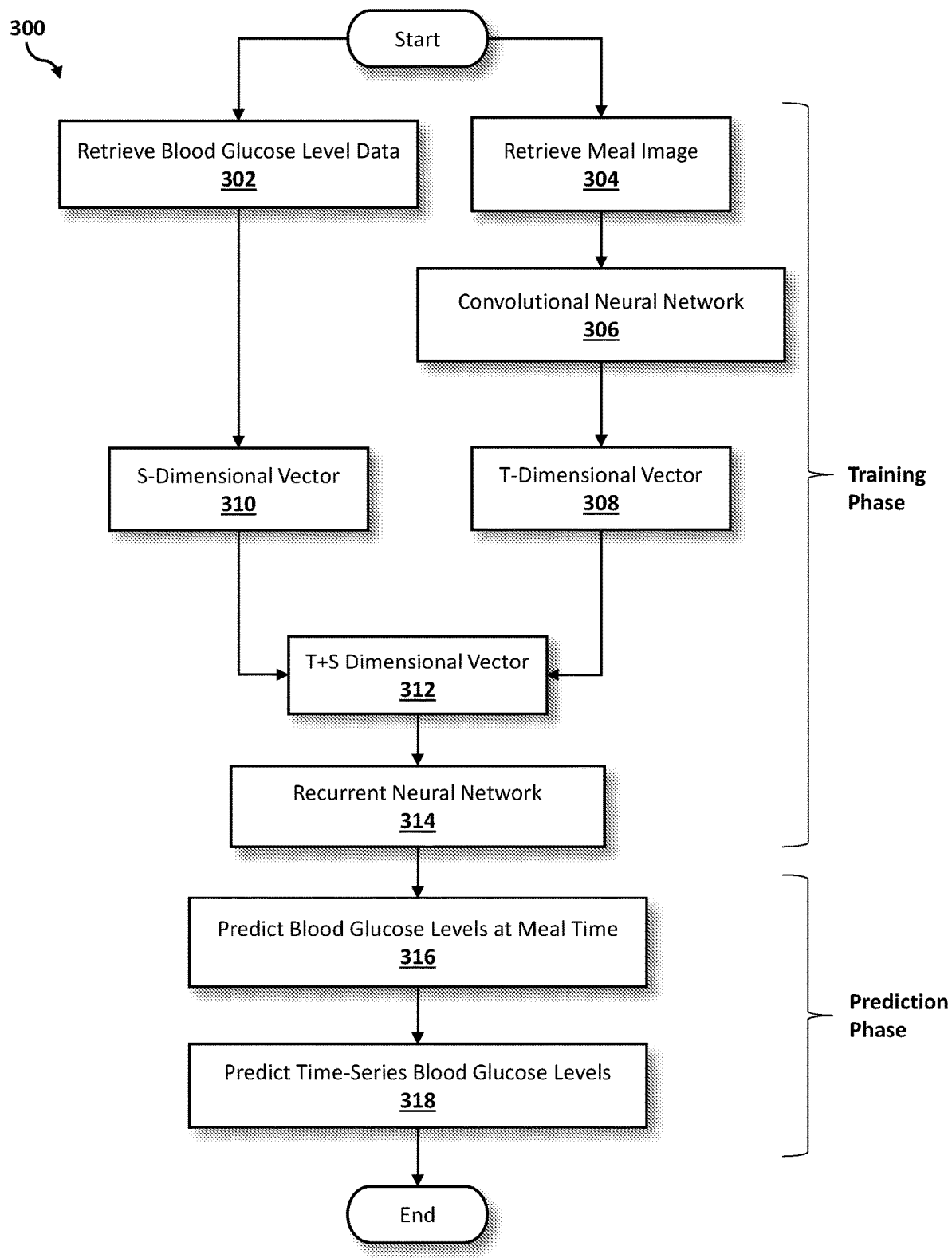
FIG. 3 is an operational flowchart illustrating a process for estimating blood glucose levels utilizing meal images by utilizing deep learning networks according to at least one embodiment.

Referring now to FIG. 3, an operational flowchart illustrating the exemplary use of deep learning networks (i.e., CNN and RNN) in the image-based blood-sugar estimation process 300 used by the image-based blood-sugar estimation program 110a, 110b according to at least one embodiment is depicted.

During the training phase, the image-based blood-sugar estimation program 110a, 110b simultaneously retrieves blood glucose level data at 302, while at least one meal image is retrieved at 304. The at least one meal image may correspond with a specific meal consumed by the past user. Similar to 204, the image-based blood-sugar estimation program 110a, 110b may utilize a software program 108 on the user device (e.g., user computer 102) to manually or automatically upload meal images associated with the meal consumed along with the CGM data. The CGM data may be retrieved from a continuous blood glucose level monitoring device associated with the user.

In another embodiment, the image-based blood-sugar estimation program 110a, 110b may retrieve the blood glucose level data and the at least one meal image consecutively. For example, the image-based blood-sugar estimation program 110a, 110b may retrieve the blood glucose level data at 302 before the at least one meal image at 304, or the image-based blood-sugar estimation program 110a, 110b may retrieve the at least one meal image at 304 before the blood glucose level data at 302.

For example, User B is a diabetic who has a continuous blood glucose level monitoring device affixed to User B. As such, during pre-determined time intervals (every two hours), the continuous blood glucose level monitoring device tests the blood glucose levels of User B and uploads the tested blood glucose levels to a software program on the smart watch and laptop of User B. For breakfast at 8:35 AM, User B consumed a full stack of five pancakes with maple syrup and butter, two chicken sausages and a small bowl of fruit with a large cup of coffee without cream or sugar.

Shortly after completing breakfast, User B uploads meal images of the pancakes, chicken sausages, fruit bowl and large cup of coffee into the image-based blood-sugar estimation program 110a, 110b by taking the meal images on User B's smart phone and then uploading the meal images into the image-based blood-sugar estimation program 110a, 110b. Then, at 10:00 AM, the continuous blood glucose level monitoring device attached to User B reads a blood glucose level of 87 mg/dl for User B, and that tested blood glucose level is uploaded into the image-based blood-sugar estimation program 110a, 110b.

Then, at 306, the retrieved meal image(s) is uploaded as input into the convolutional neural network (CNN). The CNN may classify or cluster the meal image, and algorithms may be utilized to recognize a specific meal based on the meal image provided by the user, and to associate caloric content, carbohydrate content, lipid content, protein content, and other nutritional content that affects the blood glucose levels of a user, with the meal image. The CNN may then utilize the meal images as a matrix based on the pixel values. The size of the matrix may be determined based on features associated with the width, height and color channels of each meal image. The CNN may then extract features from the meal image matrix. Then, at 308, the CNN may yield, as an output, a feature vector (i.e., T-dimensional vector or first vector, which represents CGM data or blood glucose level prediction data at times t−1, t−2, t−3). The CNN may be utilized to provide data on how each meal affects the blood glucose levels of the user.

Continuing the previous example, the meal images of User B's breakfast (pancakes, chicken sausages, small fruit bowl and large cup of coffee) that were uploaded into the image-based blood-sugar estimation program 110a, 110b were then entered as input into a CNN which classifies the meal images and uses the meal images as a matrix. The CNN uses the matrix to identify the nutritional content of the meals depicted in the meal images, and the predicted data from t−1, t−2 and t−3 are released as output from the CNN, namely 100 mg/dl, 95 mg/dl and 120 mg/dl. These outputs represent the CGM data from past users who ate similar or the same meals depicted in the meal images.

Then, at 310, the blood glucose level data retrieved at 302 is normalized into a S-dimensional vector (i.e., second vector, which represents information related to an increase of blood glucose level estimated from at least one meal image (e.g., carbohydrate content, lipid content, protein content)). The image-based blood-sugar estimation program 110a, 110b may transform the blood glucose level data into a S-dimensional vector by arranging the blood glucose level data in times series order. The T-dimensional and S-dimensional vectors may be calculated with algorithms associated with the CNN and recurrent neural network (RNN). The T-dimensional and S-dimensional vectors may then be merged (i.e., combined) thereby creating a T+S dimensional vector (i.e., third vector) at 312, and received as input into the RNN at 314. The RNN may exhibit temporal dynamic behavior of a time sequence by utilizing internal state (e.g., memory) to process sequences of inputs. The RNN may utilize connections between nodes organized in successive layers to form a directed graph along a sequence to create hidden nodes (i.e., that modify data en route from input to output), output nodes (i.e., yielding results), and input nodes (i.e., receiving data from outside the network), and each connection may have a modifiable real-valued weight. The RNN may be utilized to extract features of time-series change for the T-dimensional and S-dimensional vectors.

The RNN may be utilized to provide data on how meals and prior blood glucose levels sequentially affect the blood glucose levels of the user.

Continuing the previous example, the image-based blood-sugar estimation program 110a, 110b then uses the RNN to analyze the meal images uploaded by User B and the CGM data released as output of the CNN to determine the sequential blood glucose levels for User B. Specifically, the RNN analyzes the pancakes including the amount of individual pancakes, the type of pancakes (such as Vegan, blueberry or buttermilk) the size of the pancakes, the condiments added to the pancakes (such as maple syrup, fruit based syrup, butter, margarine), the chicken sausages including type of chicken sausages (such as white meat only), amount of chicken sausages, the condiments (if any) added to the chicken sausages, the fruit bowl including the type of fruit in the bowl, the amount of each individual fruit, whether the fruit was fresh, and the cup of coffee including the size of the coffee and what is added to the coffee (such as milk, creamer, sugar, sweetener). The nutritional content of each item in the meal image is analyzed based on CGM data to determine the possible blood glucose level of User B when the meal was consumed.

During the prediction phase, the image-based blood-sugar estimation program 110a, 110b predicts the blood glucose levels at meal time at 316 as outputs of the training phase by using machine learning. As such, the image-based blood-sugar estimation program 110a, 110b may be able to determine the blood glucose levels of the user, when the user consumed the meal indicated (t) by the meal images retrieved at 304. Then, at 318, the image-based blood-sugar estimation program 110a, 110b predicts the time-series (t+1) blood glucose levels associated with each user. The data on how meals and prior blood glucose levels sequentially affect blood glucose levels of the user, algorithms, and other data generated on meal images or the CGM data associated with the user or past users may be utilized to predict the t+1 blood glucose levels associated with each user.

Continuing the previous example, based on the CGM data and the analysis of the meal images by the RNN, the image-based blood-sugar estimation program 110a, 110b predicts, due to the high lipid content and carbohydrate content of the pancakes, the high sugar content of the fruit bowl, and the high lipid content of the chicken sausage, that the predicted blood glucose levels of User B at the time of consumption (t) of the breakfast was 102 mg/dl, and the t+1 of User B would be 115 mg/dl.

The functionality of a computer may be improved by the image-based blood-sugar estimation program 110a, 110b because the image-based blood-sugar estimation program 110a, 110b may predict sequential variation by applying RNN to train the predictor. Additionally, the image-based blood-sugar estimation program 110a, 110b may incorporate image information into the prediction of sequential variation of data measured by a measurement instrument, by inputting intermediate data, into which image information is vectorized by a CNN, and an actual measurement data of the measurement information to a RNN.

It may be appreciated that FIGS. 2 and 3 provide only an illustration of one embodiment and do not imply any limitations with regard to how different embodiments may be implemented. Many modifications to the depicted embodiment(s) may be made based on design and implementation requirements.

Figure 4:
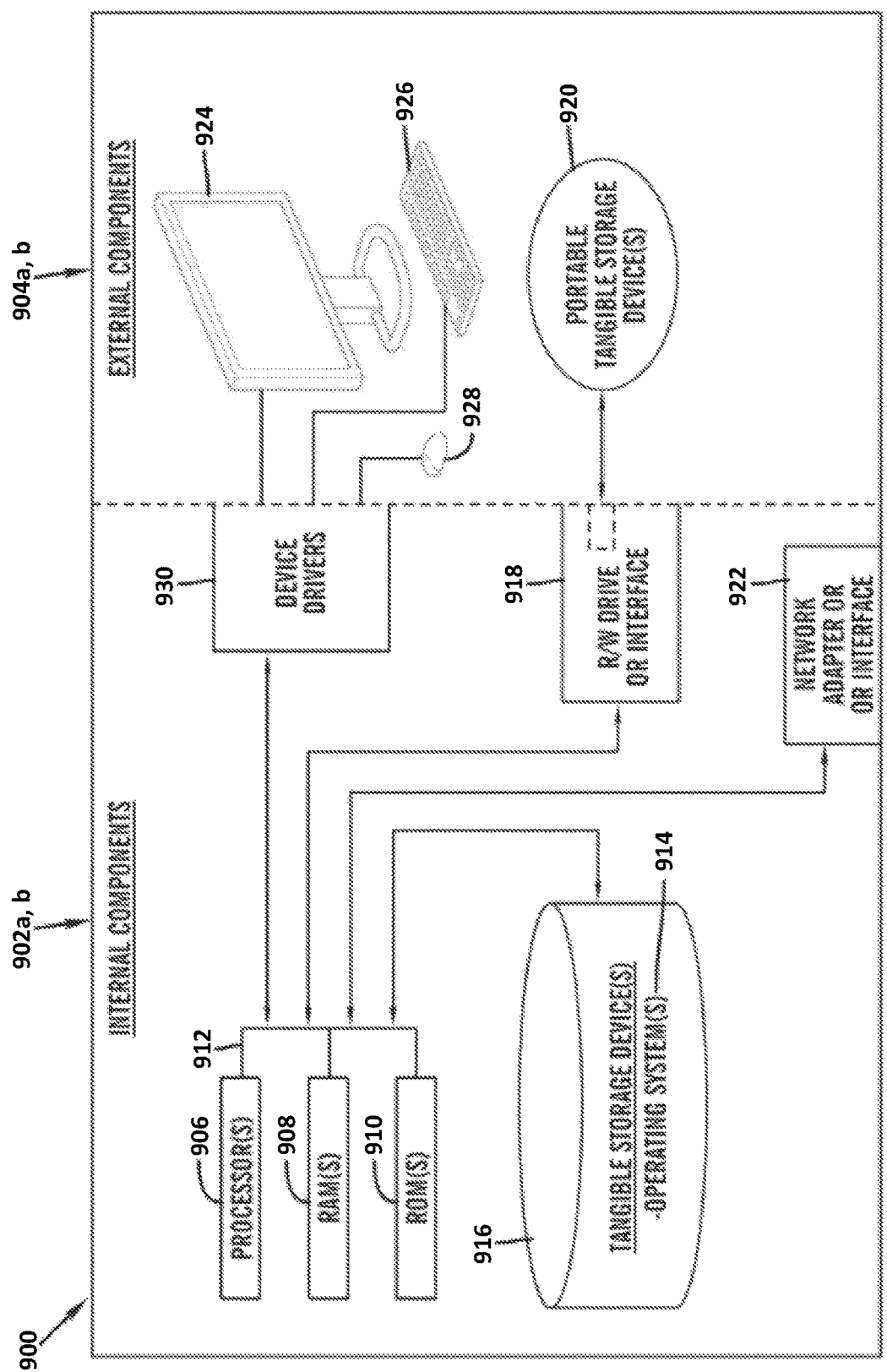
FIG. 4 is a block diagram of internal and external components of computers and servers depicted in FIG. 1 according to at least one embodiment.

FIG. 4 is a block diagram 900 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902a, b and external components 904a, b illustrated in FIG. 4. Each of the sets of internal components 902a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the image-based blood-sugar estimation program 110a in client computer 102, and the image-based blood-sugar estimation program 110b in network server 112, may be stored on one or more computer-readable tangible storage devices 916 for execution by one or more processors 906 via one or more RAMs 908 (which typically include cache memory). In the embodiment illustrated in FIG. 4, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the image-based blood-sugar estimation program 110a, 110b can be stored on one or more of the respective portable computer-readable tangible storage devices 920, read via the respective R/W drive or interface 918 and loaded into the respective hard drive 916.

Each set of internal components 902a, b may also include network adapters (or switch port cards) or interfaces 922 such as a TCP/IP adapter cards, wireless Wi-Fi interface cards, or 3G or 4G wireless interface cards or other wired or wireless communication links. The software program 108 and the image-based blood-sugar estimation program 110a in client computer 102 and the image-based blood-sugar estimation program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the image-based blood-sugar estimation program 110a in client computer 102 and the image-based blood-sugar estimation program 110b in network server computer 112 are loaded into the respective hard drive 916. The network may comprise copper wires, optical fibers, wireless transmission, routers, firewalls, switches, gateway computers and/or edge servers.

Each of the sets of external components 904a, b can include a computer display monitor 924, a keyboard 926, and a computer mouse 928. External components 904a, b can also include touch screens, virtual keyboards, touch pads, pointing devices, and other human interface devices. Each of the sets of internal components 902a, b also includes device drivers 930 to interface to computer display monitor 924, keyboard 926 and computer mouse 928. The device drivers 930, R/W drive or interface 918, and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
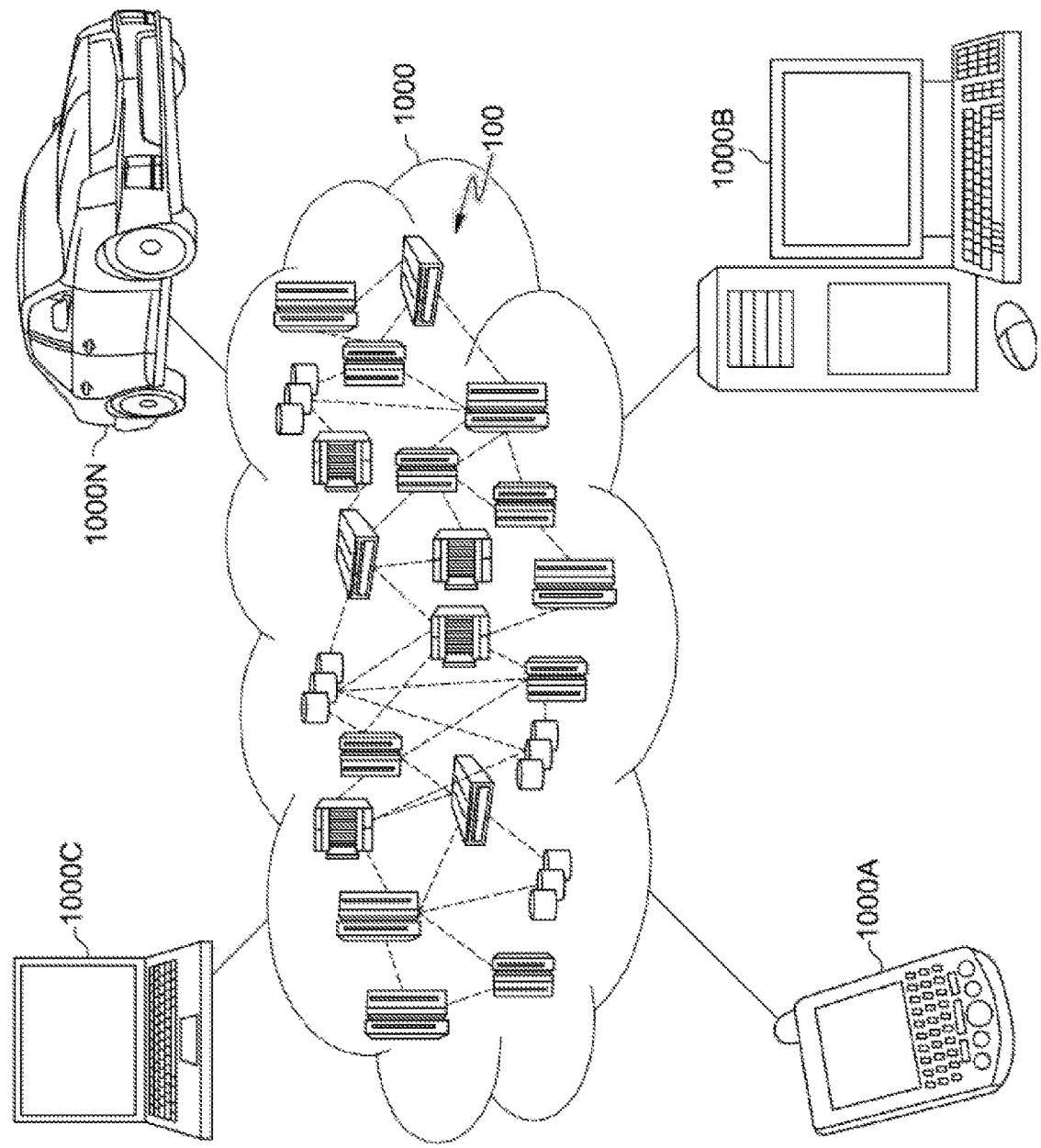
FIG. 5 is a block diagram of an illustrative cloud computing environment including the computer system depicted in FIG. 1, in accordance with an embodiment of the present disclosure.

Referring now to FIG. 5, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 5 are intended to be illustrative only and that computing nodes 100 and cloud computing environment 1000 can communicate with any type of computerized device over any type of network and/or network addressable connection (e.g., using a web browser).

Figure 6:
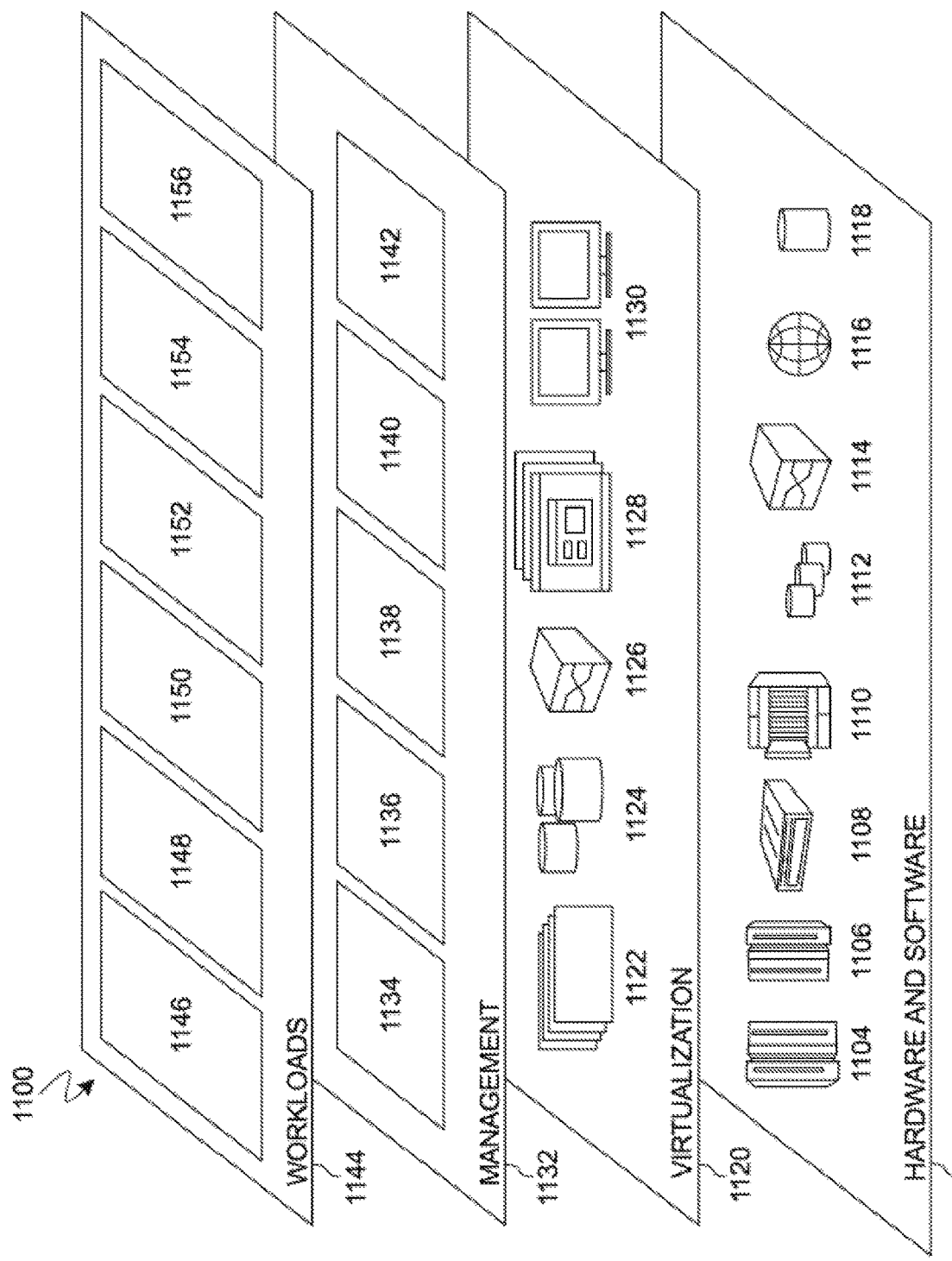
FIG. 6 is a block diagram of functional layers of the illustrative cloud computing environment of FIG. 5, in accordance with an embodiment of the present disclosure.

Referring now to FIG. 6, a set of functional abstraction layers 1100 provided by cloud computing environment 1000 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and image-based blood-sugar estimation 1156. An image-based blood-sugar estimation program 110a, 110b provides a way to estimate glucose levels in a person's blood by using meal images.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for predicting a variation of sequential blood glucose levels by using deep learning, the method comprising:
    training a predictor associated with a user by using a deep learning network;
    predicting a plurality of sequential blood glucose levels by the trained predictor based on at least one meal image, at least one time-period, and at least one set of data associated with a plurality of blood glucose levels of the user;
    displaying the predicted plurality of sequential blood glucose levels to the user;
    in response to determining a predicted plurality of sequential blood glucose levels that differ from a previously determined normal range associated with the user, alerting the user, and at least one other person; and
    storing the displayed plurality of sequential blood glucose levels with the corresponding at least one meal image and the at least one set of data associated with a plurality of blood glucose levels in a database.

2. The method of claim 1, wherein training the predictor associated with the user by using the deep learning network, further comprises:
    creating a first vector associated with the plurality of blood glucose levels associated with the user;
    creating a second vector associated with a set of information associated with an increase of the plurality of blood glucose levels associated with the user based on the at least one meal image by utilizing a convolutional neural network; and
    creating a third vector by concatenating the created first vector and the created second vector, wherein the created third vector is received as an input into a recurrent neural network.

3. The method of claim 2, wherein the plurality of blood glucose levels associated with the user includes at least one of the following:
    i. a set of data associated with continuous glucose monitoring, and
    ii. a set of data associated with previously predicted blood glucose levels.

4. The method of claim 1, further comprising:
    in response to determining a failure of the user to include the plurality of blood glucose levels associated with the user, predicting the plurality of sequential blood glucose levels by the trained predictor based on the at least one meal image and the at least one time-period.

5. The method of claim 1, wherein the at least one other person is selected from one of the following:
    i. a medical professional associated with the user,
    ii. a person closely associated with the user, and
    iii. a health care proxy agent.

6. The method of claim 1, wherein training the predictor associated with the user by using the deep learning network, further comprises:

analyzing a plurality of feedback provided by the user; and in response to determining the analyzed plurality of feedback affects the trained predictor, incorporating the analyzed plurality of feedback into a training phase associated with the trained predictor.

7. The method of claim 6, further comprising:

storing the incorporated plurality of feedback in a database; and deleting the stored plurality of feedback at previously determined time.

8. A computer system for predicting a variation of sequential blood glucose levels by using deep learning, comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

training a predictor associated with a user by using a deep learning network;

predicting a plurality of sequential blood glucose levels by the trained predictor based on at least one meal image, at least one time-period, and at least one set of data associated with a plurality of blood glucose levels of the user; and displaying the predicted plurality of sequential blood glucose levels to the user;

in response to determining a predicted plurality of sequential blood glucose levels that differ from a previously determined normal range associated with the user, alerting the user, and at least one other person; and storing the displayed plurality of sequential blood glucose levels with the corresponding at least one meal image and the at least one set of data associated with a plurality of blood glucose levels in a database.

9. The computer system of claim 8, wherein training the predictor associated with the user by using the deep learning network, further comprises:

creating a first vector associated with the plurality of blood glucose levels associated with the user;

creating a second vector associated with a set of information associated with an increase of the plurality of blood glucose levels associated with the user based on the at least one meal image by utilizing a convolutional neural network; and creating a third vector by concatenating the created first vector and the created second vector, wherein the created third vector is received as an input into a recurrent neural network.

10. The computer system of claim 9, wherein the plurality of blood glucose levels associated with the user includes at least one of the following:

i. a set of data associated with continuous glucose monitoring, and ii. a set of data associated with previously predicted blood glucose levels.

11. The computer system of claim 8, further comprising:

in response to determining a failure of the user to include the plurality of blood glucose levels associated with the user, predicting the plurality of sequential blood glucose levels by the trained predictor based on the at least one meal image and the at least one time-period.

12. The computer system of claim 8, wherein the at least one other person is selected from one of the following:

i. a medical professional associated with the user, ii. a person closely associated with the user, and iii. a health care proxy agent.

13. The computer system of claim 8, wherein training the predictor associated with the user by using the deep learning network, further comprises:

analyzing a plurality of feedback provided by the user; and in response to determining the analyzed plurality of feedback affects the trained predictor, incorporating the analyzed plurality of feedback into a training phase associated with the trained predictor.

14. The computer system of claim 13, further comprising:

storing the incorporated plurality of feedback in a database; and deleting the stored plurality of feedback at previously determined time.

15. A computer program product for predicting a variation of sequential blood glucose levels by using deep learning, comprising:

one or more non-transitory computer-readable storage media having software stored thereon with program instructions stored on at least one of the one or more tangible storage media, the program instructions executable by a processor to cause the processor to perform a method comprising:

training a predictor associated with a user by using a deep learning network;

predicting a plurality of sequential blood glucose levels by the trained predictor based on at least one meal image, at least one time-period, and at least one set of data associated with a plurality of blood glucose levels of the user;

displaying the predicted plurality of sequential blood glucose levels to the user;

in response to determining a predicted plurality of sequential blood glucose levels that differ from a previously determined normal range associated with the user, alerting the user, and at least one other person; and storing the displayed plurality of sequential blood glucose levels with the corresponding at least one meal image and the at least one set of data associated with a plurality of blood glucose levels in a database.

16. The computer program product of claim 15, wherein training the predictor associated with the user by using the deep learning network, further comprises:

creating a first vector associated with the plurality of blood glucose levels associated with the user;

creating a second vector associated with a set of information associated with an increase of the plurality of blood glucose levels associated with the user based on the at least one meal image by utilizing a convolutional neural network; and creating a third vector by concatenating the created first vector and the created second vector, wherein the created third vector is received as an input into a recurrent neural network.

17. The computer program product of claim 16, wherein the plurality of blood glucose levels associated with the user includes at least one of the following:

i. a set of data associated with continuous glucose monitoring, and ii. a set of data associated with previously predicted blood glucose levels.

18. The computer program product of claim 15, further comprising:

in response to determining a failure of the user to include the plurality of blood glucose levels associated with the user, predicting the plurality of sequential blood glucose levels by the trained predictor based on the at least one meal image and the at least one time-period.

19. The computer program product of claim 15, wherein the at least one other person is selected from one of the following:
   i. a medical professional associated with the user,
   ii. a person closely associated with the user, and
   iii. a health care proxy agent.

20. The computer program product of claim 15, wherein training the predictor associated with the user by using the deep learning network, further comprises:
   analyzing a plurality of feedback provided by the user; and
   in response to determining the analyzed plurality of feedback affects the trained predictor, incorporating the analyzed plurality of feedback into a training phase associated with the trained predictor.

21. The computer program product of claim 20, further comprising:
   storing the incorporated plurality of feedback in a database; and
   deleting the stored plurality of feedback at previously determined time.

* * * * *